US007477385B2

(12) United States Patent
Lotz et al.

(10) Patent No.: US 7,477,385 B2
(45) Date of Patent: Jan. 13, 2009

(54) METHOD OF DETERMINING PHYSICAL PROPERTIES OF AN OPTICAL LAYER OR LAYER SYSTEM

(75) Inventors: Hans-Georg Lotz, Gründau-Rothenbergen (DE); Jürgen Schroeder, Großkrotzenburg (DE)

(73) Assignee: Applied Materials GmbH & Co. KG (DE)

( * ) Notice: Subject to any disclaimer, the term of this patent is extended or adjusted under 35 U.S.C. 154(b) by 477 days.

(21) Appl. No.: 11/215,879

(22) Filed: Aug. 30, 2005

(65) Prior Publication Data

US 2006/0007430 A1 Jan. 12, 2006

(30) Foreign Application Priority Data

Jul. 9, 2004 (EP) .................................. 04021243

(51) Int. Cl.
*G01J 4/00* (2006.01)
*G01B 11/28* (2006.01)
(52) U.S. Cl. ........................................ 356/364; 356/630
(58) Field of Classification Search ................. 356/364, 356/630, 128; 250/559.27
See application file for complete search history.

(56) References Cited

U.S. PATENT DOCUMENTS 5,493,401 A 2/1996 Horie et al.

| | | | |
|---|---|---|---|
| 5,999,267 A | 12/1999 | Zawaideh et al. | |
| 6,233,046 B1 | 5/2001 | Alba et al. | |
| 6,485,872 B1 | 11/2002 | Rosenthal et al. | |
| 6,618,154 B2 | 9/2003 | Engel et al. | |
| 6,826,511 B2 | 11/2004 | Mikkelsen et al. | |
| 7,280,208 B2 * | 10/2007 | Funakubo et al. | ........... 356/364 |
| 2003/0147085 A1 | 8/2003 | Mikkelsen et al. | |

FOREIGN PATENT DOCUMENTS

| EP | 0 644 399 | 3/1995 |
|---|---|---|
| EP | 0644399 | 3/1995 |
| KR | 10-2003-0025891 | 3/2003 |
| TW | 504565 | 10/2002 |

* cited by examiner

*Primary Examiner*—Roy M Punnoose
(74) *Attorney, Agent, or Firm*—Sheridan Ross P.C.

(57) ABSTRACT

The present invention relates to a method of determining physical properties of an optical layer or layer system by means of spectral transmission and/or reflection measurements, whereby in accordance with the spectrum of the transmission and/or reflection measurement, reference values for the wavelength-dependent refractive indices $n_0$ and/or extinction coefficients $k_0$ are chosen from known values or are determined experimentally and the variation that characterizes the layer is described by wavelength-independent variation constants $K_n$ and $K_k$ for the refractive indices and extinction coefficients.

12 Claims, 2 Drawing Sheets

ITO
Thickness-Distribution

Si
Thickness-Distribution

METHOD OF DETERMINING PHYSICAL PROPERTIES OF AN OPTICAL LAYER OR LAYER SYSTEM

This application claims priority, pursuant to 35 USC § 119, to European Patent Application No. 04021243, filed Sep. 7, 2004, which is incorporated in is entirety by reference herein.

FIELD OF THE INVENTION

The present invention relates to a method of determining physical properties of an optical layer or layer system with a transmission and/or reflection measurement.

BACKGROUND OF THE INVENTION

The coating of substrates, particularly glass substrates that have optically effective layers, is wide spread. Examples include so-called low-E or thermal insulation layers for architectural glazing, antireflective layers such as for VDUs and the like. Such layers are deposited for example by sputtering techniques under vacuum conditions, it being preferable, for economic reasons, to use substrates which cover a large surface area.

In this regard, it is important that the quality of the deposited layers can be checked so as to ensure that the desired physical properties are obtained, particularly in a homogeneous manner, across the entire substrate surface area. Physical properties are defined here as, for example, the layer thickness, the transmittance or reflectance, the refractive index and the like.

The prior art, for instance, examines the uniform layer thickness of deposited layers in that once a substrate has been appropriately prepared beforehand and after the layer has been deposited, the substrate is measured mechanically, for example by means of a profilometer. For this purpose, large substrates, such as architectural glazing, will require, for example, 2,000 measuring points spread across the substrate, which, if the measurement is taken mechanically, will mean a considerable amount of time and effort that is not, in fact, practicable.

SUMMARY OF THE INVENTION

It is therefore the object of the present invention to make available a method of determining physical properties for the purpose of characterizing layers, which method can be performed in an effective and simple manner. In particular, the method is intended to permit statements about the layer's homogeneity over the coating area. In accordance with a further aspect, the intention is to make available a method which enables the effective and rapid determination of layer thicknesses and especially of the layer thickness distribution in the case of substrates that cover a large surface area.

This object is solved by a method that comprises the features of claim 1. The subject matter of the dependent claims relates to advantageous embodiments and configurations of the invention.

The invention takes advantage of the fact that it is possible to use a variation constant $K_n$ or $K_k$ or additive constant to describe the variation in the refractive index of a layer or layer system brought about by the coating conditions in the same way as it is possible to use such a constant to describe the variation in extinction coefficient.

These variation constants $K_n$ and $K_k$ can be determined easily by subtraction of a theoretical value or reference value from a refractive index and/or extinction coefficient value which is currently being ascertained by reflection and/or transmission measurements in the case of the layer to be examined. The variation constants determined in this way are therefore a measure of the deviation of the refractive index (refractive index offset) or extinction coefficient (extinction coefficient offset) from a theoretical or reference value.

Furthermore, the deviation of the layer thickness from a target value can be represented by an additive component.

Accordingly, whenever one or more variation constants are determined at several points across the coating surface or the coated substrate surface, the variation constants will permit a statement to be made about the layer's optical homogeneity.

In a preferred embodiment or configuration of the present invention, it is possible, based on the variation constants' characterization of the layer, to use nonlinear optimization algorithms to easily determine the layer thickness and optical properties, such as the refractive index and extinction coefficient, of the layer or layer system by adjusting experimental reflection and/or transmission data and theoretical reflection and/or transmission values calculated theoretically on the basis of the layer thickness, refractive index and extinction coefficient, whereby what is brought into play for this purpose are, on the one hand, theoretical or reference values for the refractive index $n_0$ and extinction coefficient $k_0$ supplemented by the additive component of the variation constants $K_n$ and $K_k$ and, on the other hand, the expected layer thickness (target layer thickness) $d_0$ added to the variation constant $K_d$ as a starting or initial value and input quantities for the nonlinear optimization. The optimization is clearly simplified and accelerated by using the variation constants of the refractive index $K_n$ and the extinction coefficient $K_k$ as well as $K_d$ for the layer thickness instead of the variously dependent values for the refractive index and extinction coefficient themselves. The nonlinear optimization algorithms that are used for this purpose are known generally from mathematics and do not need to be explained in further detail here. Examples of these algorithms include the Nelder-Mead simplex method, Powell's algorithm or optimization by means of a genetic algorithm.

The reference or theoretical values for the refractive index $n_0$ and/or extinction coefficient $k_0$ can be determined preferably in an experimental fashion by way of spectral ellipsometry on a reference layer. In principle, however, it is also possible here to use data cited in the literature. The deviation of the optical properties of that layer which is actually present from the reference values is described by the variation constants $K_n$, $K_k$ and $K_d$, whereby the nonlinear optimization of these constants permits a simple and unequivocal estimate of those values which are actually present.

The nonlinear optimization preferably starts out from an evaluation function, for which a minimum has to be determined. The use of the additive variation constants $K_n$, $K_k$ and $K_d$ ensures that no physically nonsensical solutions are found, for example by arriving at a local minimum.

The sum of the squared distances between measured reflection and/or transmission values and theoretical reflection and/or transmission values is preferably used as an evaluation function.

The variation constant or constants is (are) preferably determined by several measurements at the same spot on the layer and by averaging, whereby the measurements are particularly taken using different wavelengths or wavelength ranges.

In accordance with a further advantageous embodiment, the nonlinear optimization for estimating the layer thickness is, moreover, modified in that a series of starting or initial values is used for the layer thickness. During optimization, this determines not only a minimum of that evaluation function which belongs to the nonlinear optimization algorithm, but also a separate minimum value for each starting or initial value, the smallest value then being chosen from among these values. In the case of considerable variations in layer thickness, as may arise whenever coatings cover a large surface area, this approach stops physically incorrect or meaningless results from being determined as a result of finding local minima of the evaluation function, and instead ensures as a result of the iteration of the initial or starting value and the selection of the absolute minimum that only physically useful solutions are found.

BRIEF DESCRIPTION OF THE DRAWINGS

Further benefits, characteristics and features of the present invention are arrived at from the following detailed description of exemplary embodiments based on the attached diagrams. The figures show the following.

DETAILED DESCRIPTION OF THE INVENTION

Figure 1:
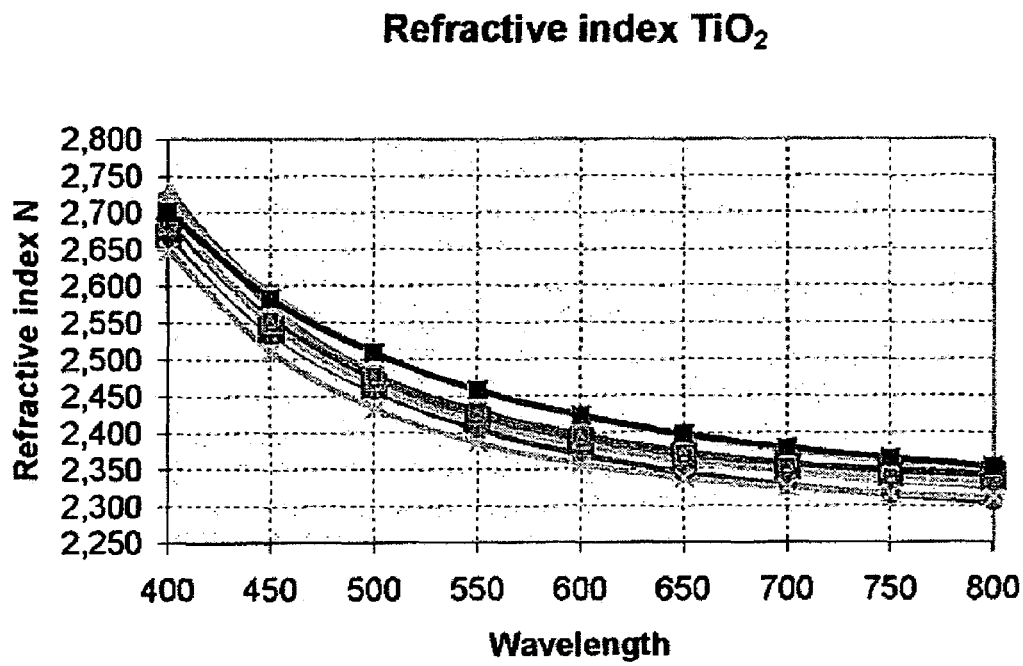
FIG. 1 depicts the refractive index n as a function of the wavelength in the case of $TiO_2$ layers that were deposited in atmospheres with different oxygen contents.

FIG. 1 depicts a diagram that illustrates the refractive index n as a function of the wavelength of the light used for a $TiO_2$ layer. The different curves are recorded for $TiO_2$ layers which were deposited under varying coating conditions with a different oxygen content in the coating atmosphere. It can be gathered from the various curves that the refractive index n, as a function of the coating conditions, is varied by an additive constant, the extent of variation being determined by the prevalent coating conditions in each case.

Figure 2:
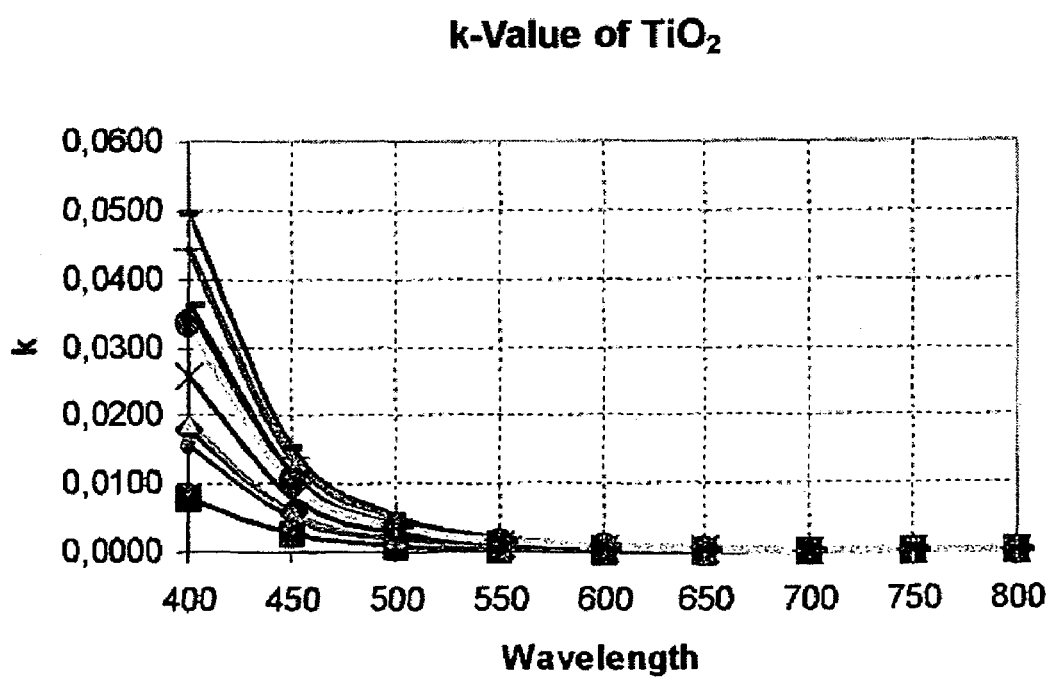
FIG. 2 depicts the extinction coefficient k as a function of the wavelength in the case of FIG. 1's $TiO_2$ layers which were deposited in atmospheres with different oxygen contents.

In the same way, FIG. 2 depicts the extinction coefficient k for various $TiO_2$ layers as a function of the wavelength of the light used. Here, too, the oxygen-induced variation in extinction coefficient for the variously deposited $TiO_2$ layers can be described by an additive constant at least in the range below a wavelength of 600 nm.

The variation in both refractive index n and extinction coefficient k, which variation is caused by different deposition conditions for the layer, can, accordingly, be described by an additive constant $K_n$ or $K_k$ respectively. The constant $K_n$ for the change in refractive index n can be easily determined in that a known (theoretical) or basically determined (reference) value for the refractive index $n_0$ is subtracted from a currently determined value for a layer that is to be examined, or several basically present or known refractive indices $n_0$ for specific wavelengths are subtracted from the currently determined values of the refractive indices n for the respective wavelengths. The basically determined reference value $n_0$ can be obtained for example by means of spectral ellipsometry. The current refractive index n for a layer that is to be examined can be determined by transmission and/or reflection measurements. A mean value for the additive constant (variation constant) can be determined on the basis of the multitude of variation constants for the different wavelengths.

Equally, a variation constant $K_k$ (additive constant) can also be determined for the extinction coefficient k, in which case values that are likewise basically known for the extinction coefficient $k_0$ of the layer to be examined are subtracted from the currently determined values of the extinction coefficient k of the layer to be examined.

The variation constants $K_n$ and $K_k$ represent a measure of the deviation of the optical properties of the coating or of the substrates covered with the coating, for example glass panes. Consequently what applies is:

$$n = n_0 + K_n$$

$$k = k_0 + K_k$$

Determination of the variation constants at a great many measurement points spread across the coated substrate, for example large-format architectural glazing, can furnish information on the homogeneity of the glass surface or coating.

According to a further aspect of the method specified by the invention, the layer thickness d is determined on the basis of the refractive index $n_0$ basically known for the layer and of the extinction coefficient $k_0$. For this purpose, nonlinear optimization algorithms are used, though only the variation constants of the refractive index $K_n$ and of the extinction coefficient $K_k$ as well as the layer thickness, which can likewise be described by means of an additive constant $K_d$ added to the target layer thickness $d_0$ ($d = d_0 + k_d$), rather than the refractive index or the extinction coefficient per se with its dependencies on various influences, are used for the purpose of optimization. As a result, a reduction of the variable parameters can be obtained, which greatly simplifies and facilitates implementation of the nonlinear optimization algorithms.

In accordance with a preferred embodiment, whenever the layer or layer system is to be examined, reflection and transmission measurements are taken at a great many points spread over the layer, with the result that data relating to reflection and transmission are obtained at each point for a specific wavelength spectrum of the light used. The known reference values for the extinction coefficient $k_0$, refractive index $n_0$ and target layer thickness $d_0$ can be used to calculate theoretical reflection and transmission values for the various wavelengths of the wavelength spectrum. Nonlinear optimization algorithms can be used to adapt the theoretically calculated reflection and transmission data to the measured data, with the variations in refractive index, extinction coefficient and layer thickness being described by the additive variation constants $K_n$, $K_k$ and $K_d$. Optimization is therefore brought about in relation to the variation constants, thereby enabling those values which are actually present, especially with respect to the layer thickness, to be estimated on the basis of the variation constants.

Those optimization algorithms which are known from mathematics, such as the Nelder-Mead simplex method, Powell's algorithm or optimization by way of a genetic algorithm, can be used as nonlinear optimization techniques.

As a general principle, the nonlinear optimization is based on finding a minimum for an evaluation function that is defined, in accordance with the preferred exemplary embodiment, by the sum of the squared distances between measured reflection and/or transmission data and theoretically calculated reflection and/or transmission data, with the theoretical reflection and/or transmission data being a function of the extinction coefficient, refractive index and layer thickness into which the theoretical values or target thickness, to which the variation constants have been added, are in turn entered. Those variation constants which were ascertained as optimum ones then provide a measure of the optical quality or, when taken together with the reference values, provide an estimate of the optical properties, especially of the layer thickness, for example.

An initial or starting value for the layer thickness, the so-called target layer thickness, must be chosen for the optimization method in which nonlinear optimization algorithms are used. The method is further enhanced in that the optimization is performed for a series of starting or initial values, such as in the case of a $TiO_2$ layer or an indium tin oxide layer (ITO layer) with a series of values lying between a minimum expected value and a maximum expected value for the layer thickness. For instance, the layer thickness of an ITO layer might be expected between a minimum of 80 nm and a maximum of 200 nm, with the result that various optimizations are performed with starting values of 80, 100, 120, 140, 160, 180 and 200 nm in order then to determine the minimum of all the evaluation functions for all these starting values, thereby obtaining an optimum approximation of the layer thickness that is to be determined.

Figure 3:
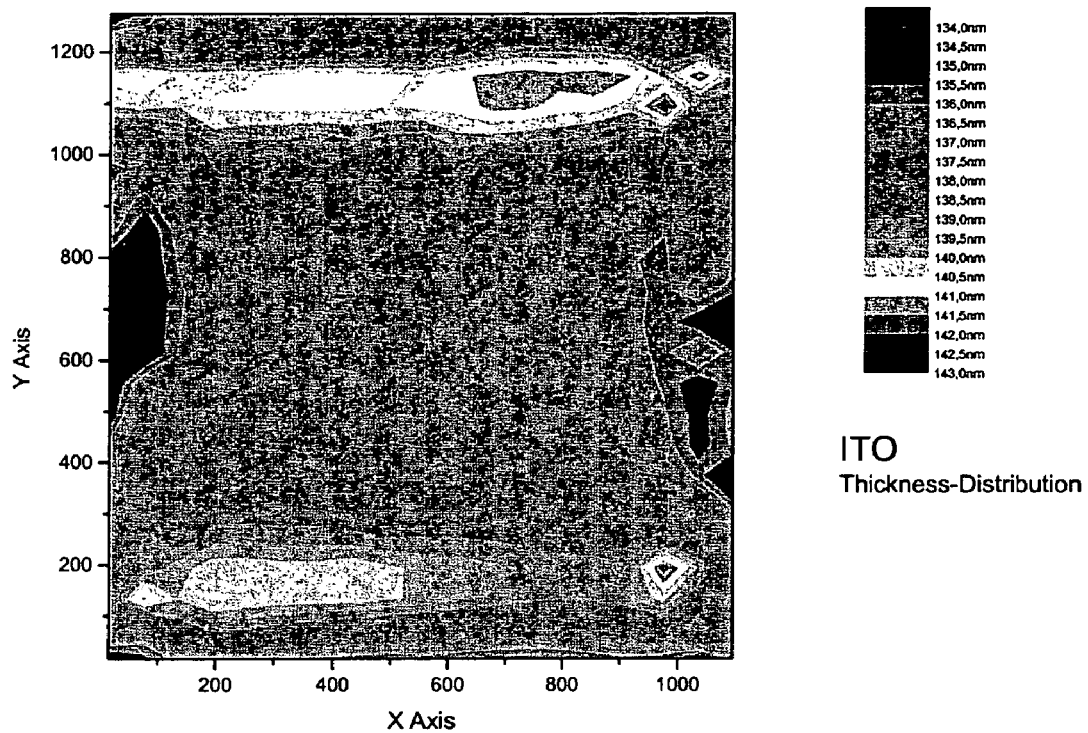
FIG. 3 depicts a diagram with the layer thickness distribution of an indium tin oxide (ITO) layer on a glass substrate.
Figure 4:
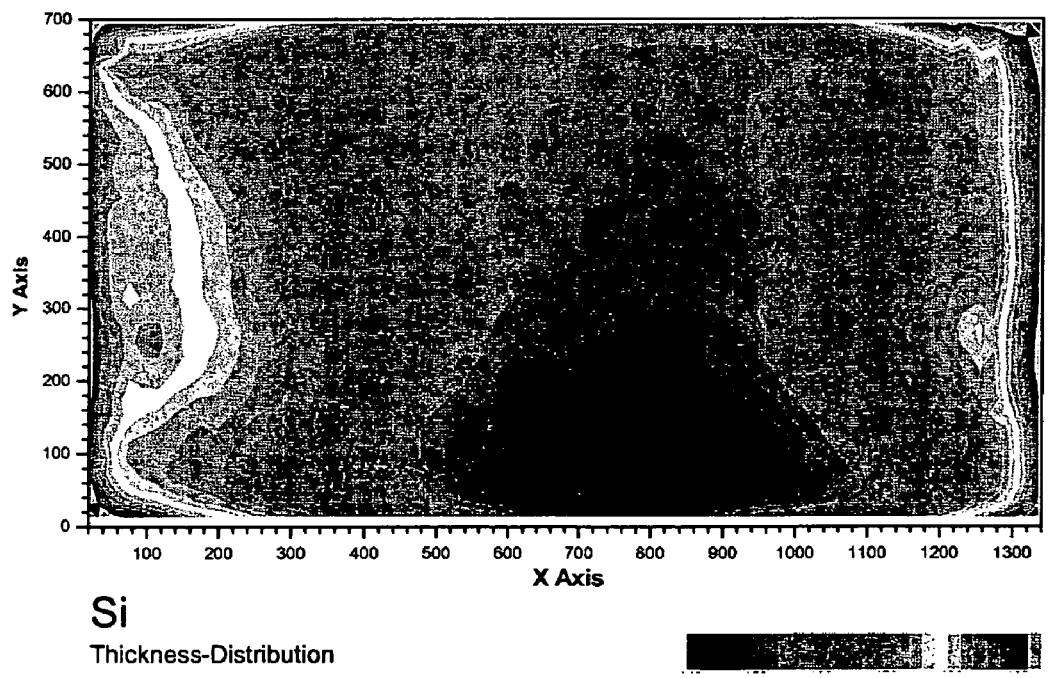
FIG. 4 depicts a diagram with a layer thickness distribution for a silicon layer on a substrate that covers a large surface area.

The diagrams in FIGS. 3 and 4 describe the result of such a determination of the layer thickness distribution over large-area glass substrates in the case of an ITO layer (FIG. 3) and a silicon layer (FIG. 4). The aforementioned substrates are over 1,000×1,200 mm and 700×1,300 mm in size respectively.

The simplified optimization by means of the variation constants $K_n$ and $K_k$ for the refractive index n and the extinction coefficient k or $K_d$ for the layer thickness d enables the layer thickness distribution to be determined rapidly as a result of many transmission and reflection measurements at a plurality of measurement points spread over the substrate surface, and this simplified optimization permits their evaluation. Furthermore, the variation constants $K_n$ and $K_k$ that were determined here provide an overview of the homogeneity of the layer's optical properties.

As is arrived at from FIGS. 3 and 4, the method according to the invention enables an automatic determination of the layer thickness, particularly if use is made of a plurality of starting or initial values for the nonlinear optimization, which avoids physically meaningless solutions, such as jumps in layer thickness that are not to be expected in physical terms. In addition, this especially applies to large-area substrates, the layer thicknesses of which may vary within a fairly large range, since the arrival at just local minima of the evaluation function, which would lead to incorrect approximations of the layer thickness, is avoided by the use of several starting or initial values for the nonlinear optimization.

What is claimed is:

1. A method for determining physical properties of an optical layer or layer system, comprising:
   selecting a reference wavelength dependent refractive index value $n_0$ and a reference extinction coefficient value $k_0$;
   measuring a refractive index n and extinction coefficient k value for the optical layer or layer system;
   calculating a wavelength-independent refractive index variation constant $K_n$ according to the equation:

$K_n = n - n_0$;

calculating a wavelength-independent extension coefficient variation constant $K_k$ according to the equation:

$K_k = k - k_0$;

displaying at least one of $K_n$ and $K_k$.

2. The method according to claim 1, further comprising:
   determining theoretical reflection and transmission values using said reference values for the refractive index $n_0$ and the extinction coefficient $k_0$, and a target value $d_0$ for a layer thickness of the optical layer or layer system; and
   adapting said theoretical values to the measured reflection and transmission values by nonlinear optimization.

3. The method of claim 2, further comprising:
   providing said reference values $n_0$, $k_0$ and $d_0$ with a variation constant $K_n$, $K_k$, and $K_d$;
   using said reference values $n_0$, $k_0$, and $d_0$ as staffing values for nonlinear optimization; and
   effecting said linear optimization in relation to said variation constants $K_n$, $K_k$, and $K_d$.

4. The method according to claim 3, further comprising determining said variation constants $K_n$, $K_k$, and $K_d$ by obtaining a plurality of measurements of a same point on the optical layer or layer system at different wavelengths.

5. The method according to claim 3, further comprising determining said variation constants $K_n$, $K_k$, and $K_d$ at a plurality of points on the optical layer or layer system to evaluate optical homogeneity over a surface area of the optical layer or layer system.

6. The method according to claim 1, further comprising determining the minimum of an evaluation function for the purpose of the nonlinear optimization.

7. The method according to claim 6, further comprising summing the squared distances between the measured reflective and transmission values and the theoretical reflective and transmission values for said evaluation function.

8. The method according to claim 7, further comprising providing a series of target layer thicknesses as a starting value to provide a minimum for the evaluation function.

9. The method according to claim 8, further comprising providing a series of values for said series of target layer thicknesses, said series of values being at intervals between a minimum thickness value and a maximum thickness value that is technically possible and expected for the optical layer or layer system.

10. The method according to claim 1, further comprising obtaining said reference values by spectral ellipsometry.

11. A non-volatile storage medium containing computer software encoded in a machine readable format for determining physical properties of an optical layer or layer system comprising:
    a set of computer instructions for selecting a reference wavelength dependent refractive index value $n_0$ and a reference extinction coefficient value $k_0$;
    a set of computer instructions for measuring a refractive index n and extinction coefficient k value for the optical layer or layer system;
    a set of computer instructions for calculating a wavelength-independent refractive index variation constant $k_n$ according to the equation:

$K_n = n - n_0$;

a set of computer instructions for calculating a wavelength-independent extension coefficient variation constant $K_k$ according to the equation:

$K_k = k - k_0$.

12. A method of determining physical properties of an optical layer or layer system, comprising:
    selecting a reference wavelength-dependent refractive index value $n_0$ and a reference extinction coefficient value $k_0$;

measuring a refractive index n and an extinction coefficient value k for the optical layer or layer system;

calculating a wavelength-independent refractive index variation constant $K_n$ according to the equation:

$$K_n = n - n_0;$$

calculating a wavelength-independent extension coefficient variation constant $K_k$ according to the equation:

$$K_k = k - k_0;$$

determining theoretical reflection and transmission values using said reference values for the refractive index $n_0$ and the extinction coefficient $k_0$, and a target value $d_0$ for a layer thickness of the optical layer or layer system;

adapting said theoretical values to the measured reflection and transmission values by nonlinear optimization;

providing said reference values $n_0$, $k_0$, and $d_0$ with a variation constant $K_n$, $K_k$, and $K_d$;

using said reference values $n_0$, $k_0$, and $d_0$ as starting values for nonlinear optimization;

effecting said linear optimization in relation to said variation constants $K_n$, $K_k$, and $K_d$; and displaying at least one of $K_n$, $K_k$ and $K_d$.

* * * * *